(12) United States Patent
Christoff

(10) Patent No.: US 7,153,130 B2
(45) Date of Patent: Dec. 26, 2006

(54) ORTHODONTIC APPLIANCE WITH REMOVABLE INSERT

(75) Inventor: James D. Christoff, Birchwood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 210 days.

(21) Appl. No.: 10/865,434

(22) Filed: Jun. 10, 2004

(65) Prior Publication Data

US 2005/0277082 A1 Dec. 15, 2005

(51) Int. Cl.
*A61C 7/00* (2006.01)
(52) U.S. Cl. ........................................................ 433/9
(58) Field of Classification Search ................ 433/8, 433/9, 11, 13, 10, 16, 17, 24, 3
See application file for complete search history.

(56) References Cited

U.S. PATENT DOCUMENTS

| | | | | |
|---|---|---|---|---|
| 2,019,773 A | * | 11/1935 | Landis ........................ 433/11 |
| 3,128,552 A | * | 4/1964 | Broussard ..................... 433/13 |
| 3,803,715 A | | 4/1974 | Wallshein | |
| 3,879,850 A | | 4/1975 | Wallshein | |
| 4,090,299 A | | 5/1978 | Williams | |
| 4,512,740 A | | 4/1985 | Kurz | |
| 4,954,080 A | | 9/1990 | Kelly et al. | |
| 5,055,039 A | | 10/1991 | Abbatte et al. | |
| 5,358,402 A | | 10/1994 | Reed et al. | |
| 5,366,372 A | | 11/1994 | Hansen et al. | |
| 5,380,196 A | | 1/1995 | Kelly et al. | |
| 5,439,379 A | * | 8/1995 | Hansen ......................... 433/8 |
| 5,542,842 A | * | 8/1996 | Andreiko et al. ............. 433/3 |
| 5,711,665 A | * | 1/1998 | Adam et al. .................. 433/9 |
| 5,863,198 A | * | 1/1999 | Doyle ........................... 433/3 |
| 5,971,754 A | * | 10/1999 | Sondhi et al. ................ 433/24 |
| 6,086,365 A | | 7/2000 | Fields | |
| 6,123,544 A | * | 9/2000 | Cleary ......................... 433/24 |
| 6,168,429 B1 | * | 1/2001 | Brown ......................... 433/11 |
| 6,309,215 B1 | * | 10/2001 | Phan et al. ................... 433/24 |
| 6,582,226 B1 | | 6/2003 | Jordan et al. | |
| 6,648,638 B1 | | 11/2003 | Castro et al. | |
| 6,705,863 B1 | | 3/2004 | Phan et al. | |
| 2002/0187451 A1 | * | 12/2002 | Phan et al. .................... 433/6 |
| 2002/0197581 A1 | * | 12/2002 | Georgakis et al. ............ 433/10 |
| 2003/0198911 A1 | * | 10/2003 | Knopp et al. ................. 433/6 |
| 2004/0048223 A1 | | 3/2004 | Phan et al. | |
| 2005/0074716 A1 | * | 4/2005 | Cleary et al. ................. 433/3 |

OTHER PUBLICATIONS

Pending U.S. Patent Application Entitled "Ceramic Orthodontic Appliance with Archwire Slot Liner"; U.S. Appl. No. 10/730,344, filed Dec. 8, 2003.
Pending U.S. Patent Application Entitled "Method and Apparatus for Indirect Bonding of Orthodontic Appliances"; U.S. Appl. No. 10/428,301, filed May 2, 2003.

(Continued)

*Primary Examiner*—Cary E. O'Connor
(74) *Attorney, Agent, or Firm*—James D. Christoff

(57) ABSTRACT

An insert is removably received in a channel of an orthodontic appliance. The insert substantially prevents sections of the appliance from moving toward each other a distance that would otherwise be sufficient for debonding the appliance from the associated tooth. The insert may be used with the appliance alone, or in combination with the appliance and a positioning tray. The insert may also be advantageously employed during manufacture, shipping, patient set-up or other handling, and may also be used in the course of treatment. Additionally, the insert may be provided with structure for serving as a positioning jig.

30 Claims, 5 Drawing Sheets

OTHER PUBLICATIONS

Pending U.S. Patent Application Entitled "Apparatus for Indirect Bonding of Orthodontic Appliances and Method of Making the Same"; U.S. Appl. No. 10/678,286, filed Oct. 3, 2003.

Pending U.S. Patent Application Entitled "Orthodontic Brace With Polymeric Arch Member"; U.S. Appl. No. 10/865,649, filed Jun. 10, 2004.

* cited by examiner

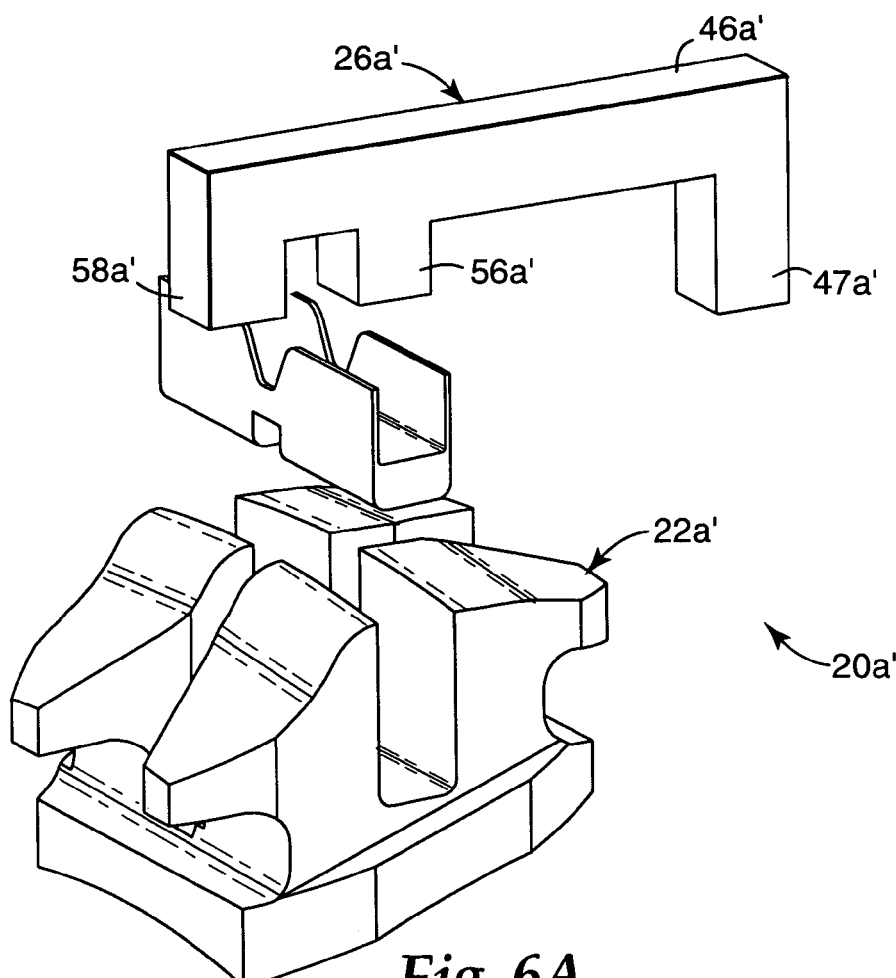
Fig. 6A
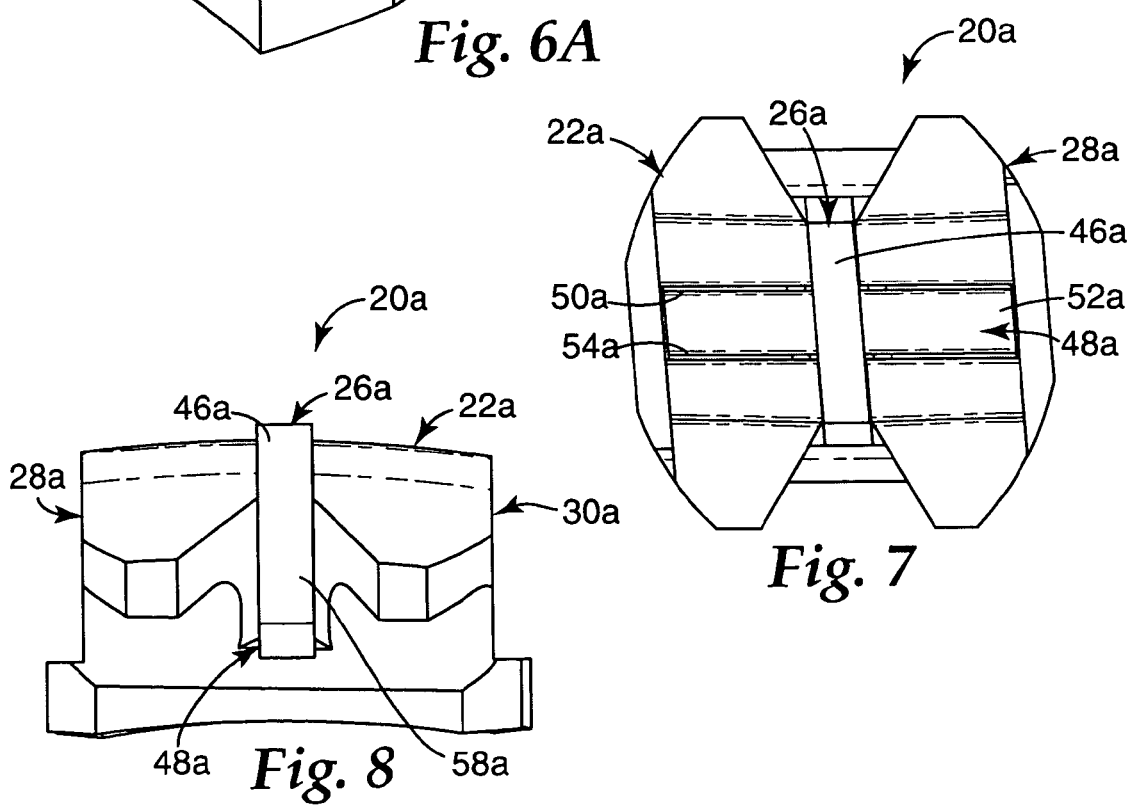
Fig. 7
Fig. 8

ORTHODONTIC APPLIANCE WITH REMOVABLE INSERT

BACKGROUND OF THE INVENTION

1. Field of the Invention

This invention broadly relates to methods and articles used in the course of orthodontic treatment. More particularly, the present invention relates to methods and articles used in conjunction with orthodontic appliances that are bonded directly to the patient's teeth.

2. Description of the Related Art

Orthodontic treatment involves movement of a dental patient's teeth to improved positions in proper alignment with each other. Orthodontic treatment can greatly enhance the patient's facial appearance, especially in regions near the front of the oral cavity. Orthodontic treatment can also improve the function of the teeth so that the opposing teeth work better with each other during mastication.

One type of common orthodontic treatment includes the use of a set of tiny appliances known as brackets. Each bracket has a slot and is affixed to one of the patient's anterior, cuspid or bicuspid teeth. Conventionally, a thin, resilient metallic archwire is received in the slots of the brackets and forms a track to guide movement of the teeth to desired positions. Ends of the archwire are often received in buccal tube appliances that are affixed to the patient's molar teeth.

Another type of common orthodontic treatment system involves a series of custom-made plastic positioning trays such as the "Invisalign" brand trays sold by Align Technology of Santa Clara, Calif. Each tray is made to move the teeth a relatively small, incremental distance toward desired final positions. The trays are made of a plastic material with sufficient resiliency to urge the teeth toward positions defined by the tray when the tray is relaxed.

However, plastic positioning trays sometimes have difficulty applying certain types of forces to teeth. For example, it is difficult for conventional positioning trays to apply a force in an extrusive direction (i.e., moving a tooth in a direction toward its outer tip). Moreover, the amount of force applied to the teeth is limited by the resiliency characteristics of the plastic material, which in general is somewhat less than can be applied to the teeth by the use of brackets and archwires.

Some orthodontic practitioners have used a "combination" treatment plan, wherein the patient is provided with a series of the plastic positioning trays at the beginning stages of treatment. Subsequently, and after the teeth are located closer to desired final positions, the use of the trays is discontinued and replaced by brackets and archwires. It is often thought that the use of brackets and archwires in the final stages of treatment provides a better result in terms of moving the teeth to exact desired positions at the conclusion of treatment.

It has also been proposed to use bonded orthodontic appliances simultaneously with plastic positioning trays. For example, U.S. Pat. Nos. 6,309,215 and 6,705,863 describe plastic positioning trays having receptacles for removably receiving appliances that are directly bonded to the patient's teeth. The bonded appliances can function as a handle to facilitate the transmission of force between the teeth and the positioning tray.

Regardless of whether or not orthodontic appliances such as brackets are used alone or in combination with a repositioning tray, it is desirable that the appliances debond easily and predictably from the teeth at the conclusion of treatment. Metal brackets, for example, are typically debonded from teeth by using a peeling or prying motion. An improved ceramic bracket having a debonding channel is described in U.S. Pat. Nos. 5,439,379 and 5,366,372, and the bracket is debonded by pivoting sections of the bracket toward each other.

However, it is also important to ensure that the orthodontic brackets do not spontaneously debond from the tooth before the practitioner intends to remove the brackets. If, for example, a bracket detaches from the tooth prior to the conclusion of treatment, the detached bracket must normally be re-bonded or replaced with a new bracket in order to resume the course of treatment. As can be appreciated, premature debonding of orthodontic brackets represents a significant nuisance to both the orthodontist and the patient that is best avoided if at all possible.

SUMMARY OF THE INVENTION

The present invention concerns an orthodontic appliance and a removable insert that is received in a channel of the appliance. Once the insert has been removed from the channel, the appliance can be debonded from the tooth by moving sections of the appliance in a direction toward the channel. However, during the time that the insert is received in the channel, the insert substantially prevents movement of the sections to an extent that would be otherwise sufficient to debond the appliance from the tooth.

Optionally, the appliance and the insert of the present invention can be used in combination with a resilient positioning tray having a receptacle for receiving the appliance. As the positioning tray exerts forces on the appliance during the course of treatment, the insert helps to reduce the risk that one or more sections of the appliance will be moved a distance sufficient to detach the appliance from the tooth.

The appliance and insert of the present invention are also useful in instances when used alone and not in combination with plastic positioning trays. For example, the invention may be advantageously employed at any stage during handling of the appliance, to help insure that the appliance is not unduly distorted in shape or fractured before treatment has concluded. For example, the insert may be used during the time that the appliance is manufactured, shipped, handled in the practitioner's office, bonded to the patient's tooth and/or used as a force member during the course of treatment.

In more detail, the present invention in one aspect is directed to an assembly that comprises an orthodontic appliance having a base for bonding the appliance to a tooth and a body extending outwardly from the base. The body includes a first section, a second section and an elongated channel extending between the first section and the second section. The appliance is debondable from the tooth by moving at least one of the first section and the second section in a direction toward the channel. The assembly also includes an insert that is removably received in the channel. The insert substantially prevents movement of the first section and the second section to an extent sufficient to debond the appliance from the tooth when the insert is received in the channel.

The present invention is also directed in another aspect to a method of orthodontic treatment. The method comprises:

bonding an appliance to a patient's tooth, wherein the appliance has a first section, a second section and an elongated channel extending between the first section and the second section;

applying force to the appliance in order to move the tooth toward a desired position;

removing an insert from the channel after the tooth has been at least partially moved toward the desired position; and debonding the appliance from the patient's tooth by moving at least one of the first section and the second section in a direction generally toward the channel.

These and other aspects of the invention are described in more detail in the paragraphs that follow and are illustrated in the accompanying drawings.

BRIEF DESCRIPTION OF THE DRAWINGS

FIG. 6a is a view somewhat similar to FIG. 6 except showing an orthodontic assembly in accordance with another embodiment of the invention;

FIG. 7 is a front elevational view of the orthodontic assembly shown in FIGS. 5 and 6, looking at the assembly in a lingual direction;

FIG. 8 is an end elevational view of the assembly shown in FIGS. 5–7, looking at the assembly in a direction toward its occlusal side;

DETAILED DESCRIPTION OF THE PREFERRED EMBODIMENTS

Figure 1:
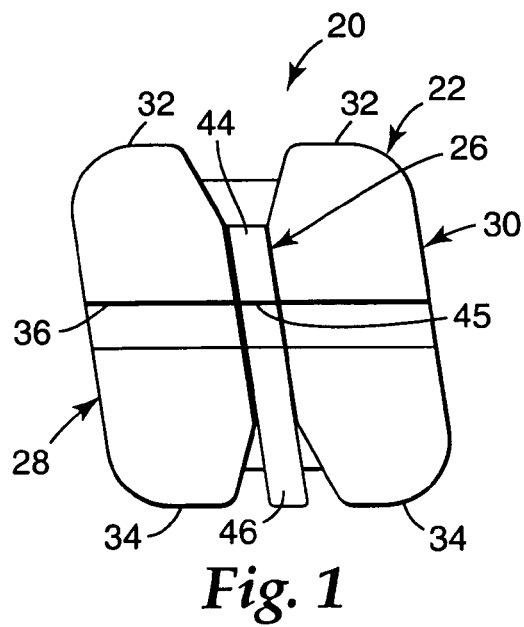
FIG. 1 is a front elevational view looking in a lingual direction toward an orthodontic assembly made in accordance with one embodiment of the invention.

An orthodontic assembly according to one embodiment of the present invention is illustrated in FIGS. 1–4 and is broadly designated by the numeral 20. The assembly 20 includes an orthodontic appliance 22 having an elongated channel 24. The assembly 20 also includes an insert 26 that is removably received in the channel 24.

In more detail, the appliance 22 includes a mesial section 28 and a distal section 30. The channel 24 extends between the mesial section 28 and the distal section 30. Each of the sections 28, 30 includes an occlusal tiewing 32 (i.e., a tiewing extending toward the outer tip of the tooth) and a gingival tiewing 34 (i.e., a tiewing extending toward the gingiva or gums). The tiewings 32, 34 extend over ligature-receiving undercuts or grooves of the appliance 22.

An archwire slot 36 extends in a generally mesial-distal direction in the mesial section 28 and the distal section 30, and preferably has spaced-apart, parallel, occlusal and gingival walls interconnected by a perpendicular bottom wall. Preferably, the walls are constructed to matingly receive an archwire having a rectangular cross-section for facilitating the transfer of forces between the archwire and the appliance 22 without undue tolerance or "slop".

The channel 24 (FIGS. 3 and 4) extends in a generally occlusal-gingival direction between the mesial section 28 and the distal section 30. As can be observed by comparing FIG. 3 with FIG. 2, the channel 24 preferably has a depth in a lingual direction (i.e., in a direction toward the patient's tongue) that is greater than the lingual depth of the archwire slot 36. In this embodiment, the channel 24 has a rectangular configuration in transverse cross-section and extends from the occlusal side to the gingival side of the appliance 22.

The mesial section 28 includes a base having an external lingual bonding surface 38. Similarly, the distal section 30 includes a base with an external lingual bonding surface 40. In this embodiment, the base of the mesial section 28 and the base of the distal section 30 are integrally connected by a thin, frangible web 42 that extends directly beneath and along the entire length of the channel 24. The web 42 overlies a groove that extends in a direction parallel to the longitudinal axis of the channel 24.

Figure 3:
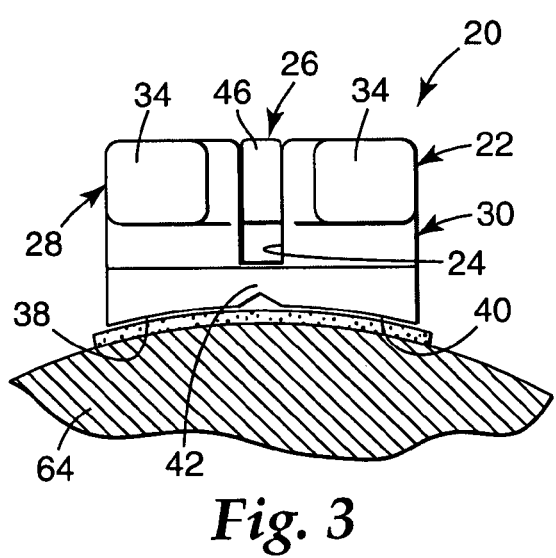
FIG. 3 is a bottom view of the assembly shown in FIG. 1, looking toward a gingival side of the assembly and showing, for illustrative purposes, the surface of the tooth upon which an appliance of the assembly is mounted.
Figure 4:
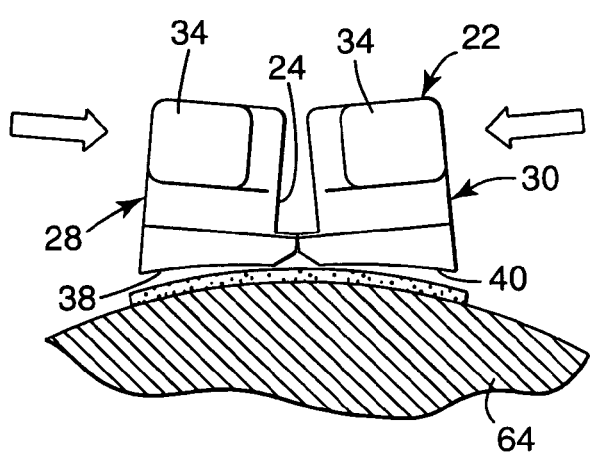
FIG. 4 is a view somewhat similar to FIG. 3 except that an insert of the assembly has been removed from the appliance and sections of the appliance have been moved toward each other in order to debond the appliance from the tooth.
Figure 5:
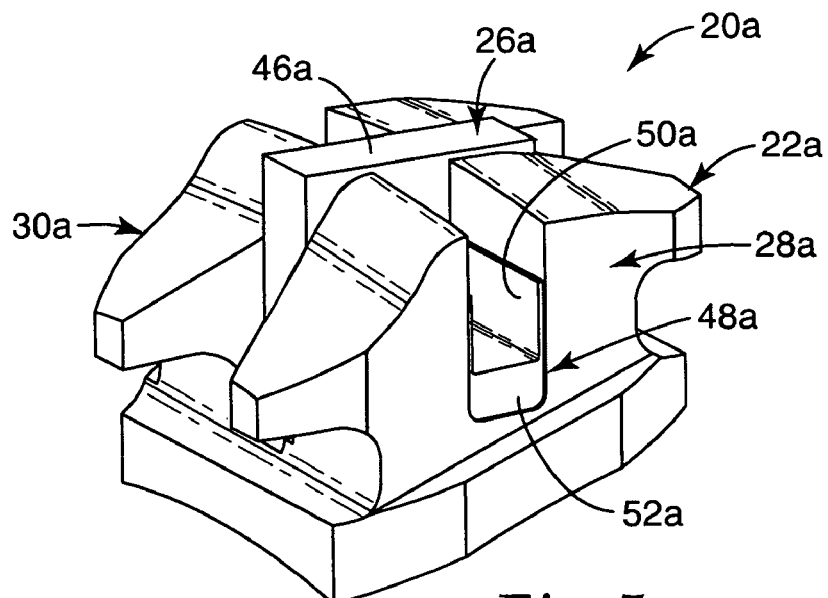
FIG. 5 is a perspective view of an orthodontic assembly according to another embodiment of the present invention, looking at the assembly toward its gingival, mesial and buccolabial sides.

As can be observed by reference to FIG. 3, the web 42 interconnects the bonding surfaces 38, 40 of the mesial and distal sections 28, 30. Preferably, the surfaces 38,40 together present a concave, compoundly curved configuration that matches the convex, compoundly curved shape of the surface of a tooth (FIGS. 3 and 4) to which the appliance 22 is adhesively bonded. Optionally, the channel 24 has a rounded bottom (not shown) to enhance fracturing of the web 42 generally in a reference plane that coincides with the central, longitudinal axis of the channel 24.

The insert 26 in this embodiment has a generally flat shape. A first portion 44 of the insert 26 is received in the channel 24. At least one region of the first portion 44 has a thickness in a mesial-distal direction that is substantially equal to the width of the channel 24 in a mesial-distal direction. For example, the first portion 44 may have a substantially rectangular cross-sectional shape as exemplified in FIG. 3 when viewed in a gingival direction. Alternatively, the first portion 44 may have a tapered shape or other shape that helps to reduce friction between the insert 26 and the sections 28, 30 when the insert 26 is removed from the channel 24. However, at least part of the first portion 44 has a shape or thickness sufficient to prevent movement of one or both of the sections 28, 30 a distance sufficient to detach one or both of the sections 28, 30 from the tooth 64 as will be described in further detail below.

Figure 2:
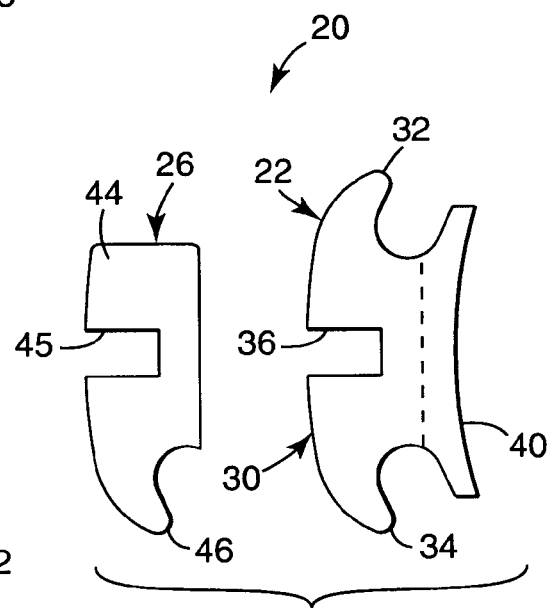
FIG. 2 is an exploded, elevational view of the assembly shown in FIG. 1, looking in a direction toward a mesial side of the assembly.

Optionally, and as shown in FIG. 2, the first portion 44 includes a notch 45 as shown in FIGS. 1 and 2. The notch 45 coincides with the archwire slot 36 when the insert 26 is received in the channel 24, so that the insert 26 may remain in place in the appliance 22 during treatment. However, the notch 45 may be omitted in instances where the insert 26 is to be removed before an archwire is placed in the archwire slot 36.

Preferably, the insert 26 also includes a second portion 46 that is integrally connected to the first portion 44. The second portion 46 extends outwardly past the confines of the channel 24 a distance sufficient to enable grasping or moving the insert 26 by a hand instrument. In the illustrated embodiment, the second portion 46 extends in a gingival direction. Alternatively, however, the second portion could extend in a buccolabial direction (i.e., in a direction toward the patient's lips or cheeks) outwardly past the buccolabial side of the appliance 22 or in an occlusal direction. As a further option, the second portion 46 may extend outwardly from the first portion 44 in two or more directions.

When the insert 26 is received in the channel 24 as shown in FIG. 3, the insert substantially prevents movement of the sections 28, 30 toward each other. To this end, the insert 24 functions as a stop to limit movement of either or both of the sections 28, 30 a distance sufficient to fracture the adhesive bond between the bonding surfaces 38, 40 respectively and the enamel surface of the tooth 64. By limiting movement of the section 28, 30, the insert 26 also helps to ensure that the web 24 does not unintentionally fracture.

When the orthodontic practitioner desires to remove the appliance 22 from the tooth 64, a hand instrument such as a ligature director or mosquito forceps is used to remove the insert 26 from the channel 24. Next, a pliers-type tool, such as the debonding tool described in U.S. Pat. Nos. 5,439,379 and 5,366,372, is used to fracture the adhesive bond between the appliance 22 and the tooth. To this end, one jaw of the pliers-like debonding tool is placed in a position to engage a mesial side of the mesial section 28 in areas adjacent to the occlusal tiewing 32 and gingival tiewing 34 of the mesial section 28, while the remaining jaw is placed to engage a distal side of the distal section 30 in areas adjacent the occlusal tiewing 32 and the gingival tiewing 34 of the distal section 30. The jaws of the tool engage the sides of the appliance 22 in buccolabial areas of the sections 28, 30, and preferably do not engage those portions of the sections 28, 30 that are located in a lingual direction relative to the bottom of the channel 24.

Next, the practitioner uses the tool to urge the engaged mesial and distal sides of the sections 28, 30 in a direction toward each other in such a manner that one or both of the sections 28, 30 pivotally move toward each other in an arc about a reference axis that is generally parallel to the longitudinal, central axis of the channel 24. As one or both of the sections 28, 30 move from the orientations shown in FIG. 3 and toward the orientations shown in FIG. 4, the web 42 fractures in the manner illustrated in FIG. 4, thereby enabling the bonding surfaces 38, 40 to detach from underlying areas of the tooth.

In this embodiment, the appliance 22 is made of a ceramic material that fractures as the sections 28, 30 are moved toward each other and toward the channel 24. Preferably, the ceramic material is a translucent or transparent ceramic material such as monocrystalline or polycrystalline alumina. Preferably, the ceramic material exhibits a light transmittance sufficient for the color of the tooth to be visible through the appliance 22 or for the appliance 22 to assume the color of the underlying tooth. Suitable polycrystalline ceramic materials are described in U.S. Pat. Nos. 4,954,080 and 6,648,638, the disclosures of which are incorporated by reference herein. In addition to polycrystalline and monocrystalline alpha-alumina, other ceramics may also be used, such as porcelain, glass, glass-ceramics and the like.

Additional aspects concerning the appliance 22 as well as other alternative constructions are set out in U.S. Pat. Nos. 5,439,379 and 5,366,372, the disclosures of which are also hereby expressly incorporated by reference herein.

Alternatively, the appliance 22 is comprised of materials other than ceramic, such as metallic materials or plastic materials. Suitable metallic materials include alloys of stainless steel, such as series 300 stainless steel and 17-4 PH stainless steel. Suitable plastic materials include polycarbonate, which is optionally reinforced with glass fibers.

The insert 26 may be made of any one of a number of materials. Preferably, the insert is made of a material that is suitable for sustained use in the oral environment and is not susceptible to significant staining by food or beverages in instances where the insert 26 is intended to remain in the channel 24 during all or a portion of treatment. Suitable materials include plastic materials such as polyurethane and polycarbonate.

Figure 6:
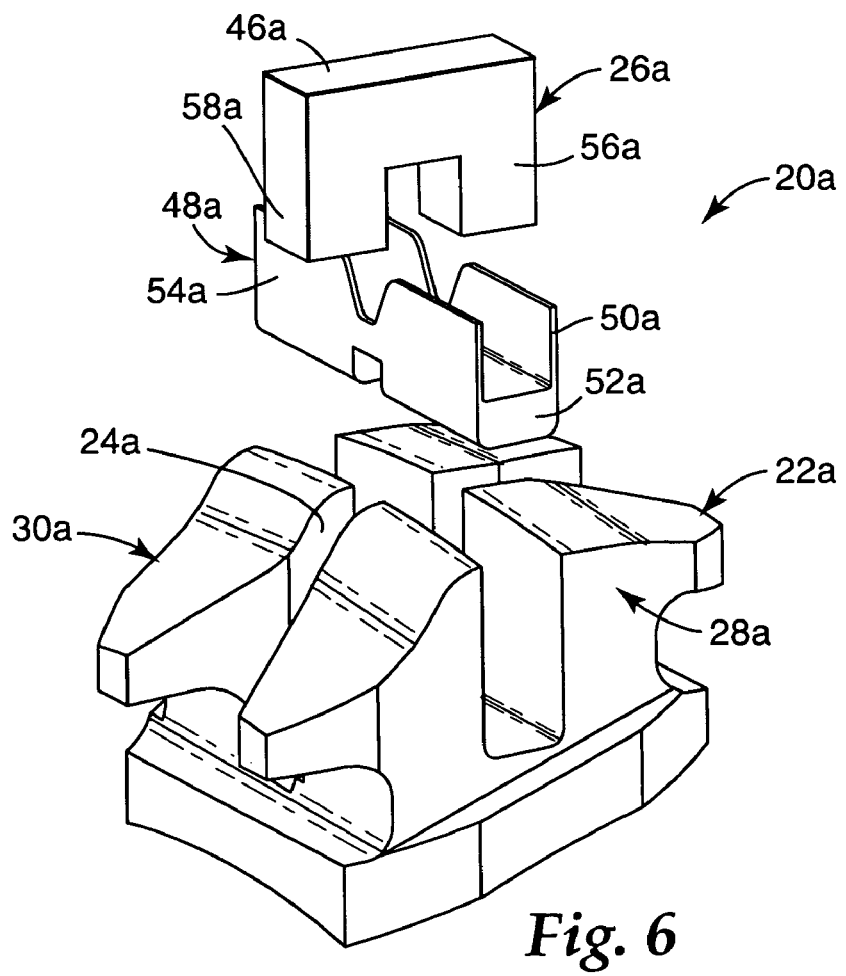
FIG. 6 is a view somewhat similar to FIG. 5 except showing the assembly in exploded view.

An orthodontic assembly 20a according to another embodiment of the invention is illustrated in FIGS. 5–8. The assembly 20a includes an appliance 22a having a channel 24a (FIG. 6). The assembly also includes an insert 26a that is removably received in the channel 24a.

The appliance 22a also includes an archwire slot liner 48a that is connected to a mesial section 28a and a distal section 30a of the appliance 22a. The archwire slot liner 48a has an occlusal section 50a, a lingual section 52a and a gingival section 54a. The occlusal section 50a and the gingival section 54a preferably extend in parallel reference planes and the lingual section 52a preferably extends in a reference plane perpendicular to the sections 50a, 54a. The sections 50a, 52a, 54a together present an overall, generally "U"-shaped configuration when viewed in directions along the longitudinal of the axis of the archwire slot liner 48a. In addition, the sections 50a, 52a, 54a together define an archwire slot for receiving an archwire (not shown in the drawings).

The archwire slot liner 48a is connected to the mesial section 28a and the distal section 38a by any one of a number of methods. For example, an adhesive, such as an epoxy or a dental or orthodontic adhesive may be used. Other methods include a soldering process, a brazing process and a glazing technique. Examples of suitable brazing processes include the processes described in U.S. Pat. Nos. 5,358,402 and 5,380,196, both of which are expressly incorporated by reference herein. An example of a suitable glazing technique involves the use of a glass paste or slurry that is heated to its softening or melting temperature.

Additional aspects and alternative constructions of the archwire slot liner 48a are described in applicant's pending U.S. Patent Publication No. 2005/0123875.

The insert 26a includes a first portion having an occlusal leg 56a and a gingival leg 58a as illustrated for example in FIG. 6. When the insert 26a is received in the channel 24a, the legs 56a, 58a straddle the archwire slot liner 48a and extend in a generally lingual direction toward the bottom of the channel 24a. Preferably, the insert 26a also includes a second portion 46a that extends beyond the buccolabial side of the appliance 22a to facilitate grasping of the insert 26a and removal from the channel 24a when desired.

Other aspects of the assembly 20 are essentially identical to the aspects of the assembly 20 described above. As such, a detailed description of the similar aspects need not be repeated.

An orthodontic assembly 20a' constructed in accordance with another embodiment of the invention is illustrated in FIG. 6A. The assembly 20a' is essentially the same as the assembly 20a except for the aspects described below.

The assembly 20a' includes an appliance 22a' as well as an insert 26a'. The insert 26a' has a first portion with an occlusal leg 56a' and a gingival leg 58'. The insert 26a' also includes a second portion 46a' that is integrally connected to the first portion.

In this embodiment, the second portion 46a' extends beyond the buccolabial side of the appliance 22a', and also extends beyond the occlusal side of the appliance 22a'. The second portion 46a' includes a leg 47a' for engagement with the outer or occlusal tip of the patient's tooth.

The length of the second portion 46a' is selected so that the appliance 22a' is properly positioned in a vertical or occlusal-gingival direction on the patient's tooth when the leg 47a' is in contact with the occlusal tip of the patient's tooth. Consequently, the insert 26a' functions as a positioning jig to facilitate bonding the appliance 22a' in a proper, pre-defined position on the tooth. Optionally, the leg 47a' may have additional structure for facilitating orientation of the appliance 22a' in a mesial-distal direction on the tooth. For example, the leg 47a' may include structure resembling a cap that matingly fits over the occlusal edge portion of the patient's tooth to provide a custom positioning jig that helps to position the appliance 22a' in both an occlusal-gingival direction as well as in a mesial-distal direction. As another option, the leg 47a' may be omitted, and the second portion may be provided with notches, index marks, shoulders or other indicia to help position the appliance 22a' in an occlusal-gingival direction relative to the occlusal edge of the tooth.

Figure 9:
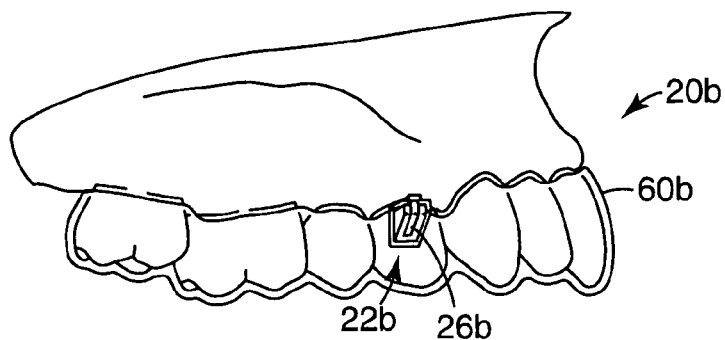
FIG. 9 is a perspective view of an orthodontic assembly according to another embodiment of the present invention, wherein the assembly includes an orthodontic appliance, a removable insert and a plastic positioning tray, and wherein also is shown an exemplary upper dental arch of an orthodontic patient undergoing treatment.

An orthodontic assembly 20b according to another embodiment of the invention is illustrated in FIG. 9. The assembly 20b includes at least one orthodontic appliance such as appliance 22b that is mounted on the patient's first bicuspid tooth. The assembly also includes an insert 26b that is received in a channel of the appliance 22b, as well as a resilient positioning tray 60b.

The resilient or elastic positioning tray 60b has a cavity or receptacle for removably receiving the appliance 22b when the tray 60b is worn over the teeth. Preferably, the position of the receptacle relative to remaining portions of the tray 60b is selected to facilitate the transfer of a force between the tooth bonded to the appliance 22b and the tray 60b. To this end, the receptacle preferably has a shape that is complemental to the exterior surface of the appliance 22b, so that force can be transferred between the appliance 22b and the tray 60b without excessive tolerance or "slop".

Preferably, the appliance 22b, the insert 26b and the tray 60b are all made of aesthetic materials that transmit light. For example, the appliance 22b may be made of a ceramic material that is translucent or transparent as mentioned above in connection with the appliance 22. The insert 26b as well as the tray 60b may be made of polymeric materials that transmit light, such that the polymeric materials mentioned above in connection with the insert 26. Suitable materials for the tray 60b include 0.03 inch thermal forming dental material, available from Tru-Tain Plastics.

Optionally, the tray 60b is one of a series of thin repositioning shells or trays representing successive stages of an orthodontic treatment program. Optionally, the tray 60b includes cavities shaped to receive and resiliently reposition teeth in incremental positions, such that the final tray moves the teeth to a final tooth arrangement. Examples of suitable positioning trays are described in U.S. Pat. Nos. 6,309,215 and 6,705,863, the disclosures of which are expressly incorporated by reference herein.

Figure 10:
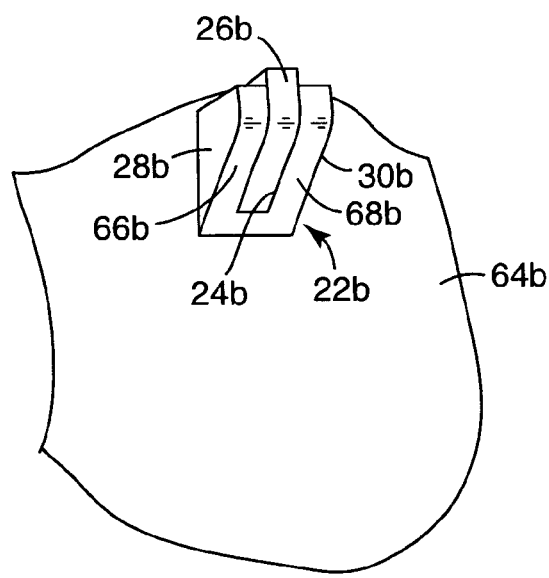
FIG. 10 is an enlarged view of a portion of the orthodontic assembly illustrated in FIG. 9.

The appliance 22b and the insert 26b are shown in enlarged view in FIG. 10. The appliance 22b includes a mesial section 28b and a distal section 30b, as well as a channel 24b that extends between the sections 28b, 30b in a generally occlusal-gingival direction. To debond the appliance 22b from a tooth such as tooth 64b, one or both of the sections 28b, 30b are moved in a direction toward the channel 24b, similar to the debonding of the appliance 22 as set out above.

As shown in FIG. 10, the appliance 22b includes a tapered occlusal side that is presented by a tapered surface 66b of the mesial section 28b and a tapered surface 68b of the distal section 30b. The tapered surfaces 66b, 68b help to seat the tray 60b into a proper position. The receptacle of the tray 60b preferably also has tapered inner surfaces that match the shape and orientation of the tapered surfaces 66b, 68b of the appliance 22b.

Figure 11:
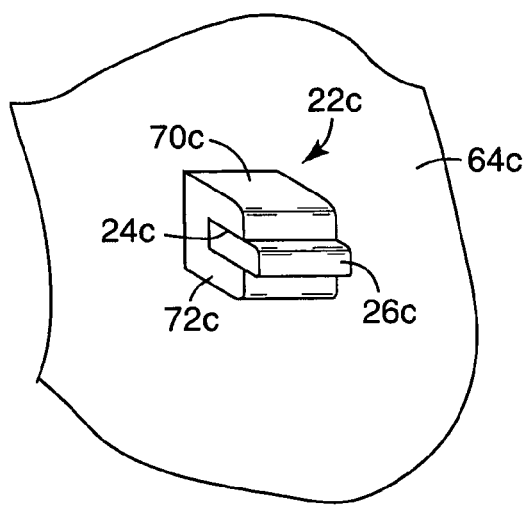
FIG. 11 is a view somewhat similar to FIG. 10 except in accordance with another embodiment of the present invention.

In FIG. 11, an orthodontic assembly includes an appliance 22c that is similar to the appliance 22b. However, the appliance 22c includes an occlusal section 70c and a gingival section 72c. A channel 24c extends in a generally mesial-distal direction between the occlusal section 70c and the gingival section 72c, and an insert 26c is removably received in the channel 24c.

When it is desired to debond the appliance 22c from the tooth (such as tooth 64c), one or both of the occlusal section 70c and the gingival section 72c are moved in a direction toward the channel 24c by exerting a force in the occlusal and/or gingival direction as desired. The appliance 22c then debonds from the tooth in a manner similar to debonding of the appliances 22, 22a, and 22b.

Other aspects of the appliances 22b, 22c and the inserts 26b, 26c are similar to the appliances 22, 22a and the inserts 26 and 26a set out above.

Figure 12:
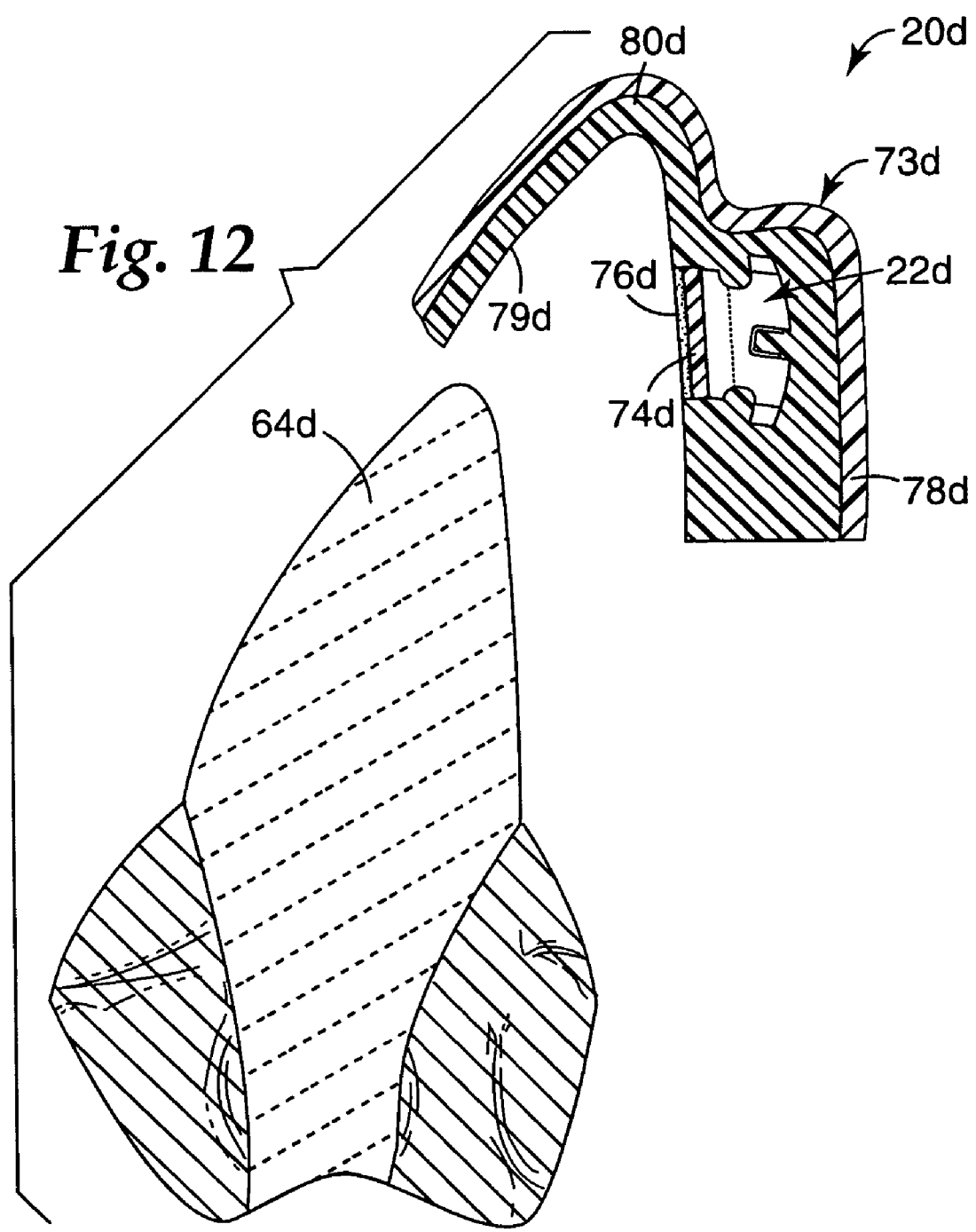
FIG. 12 is a side cross-sectional view, looking in a mesial direction, of an orthodontic assembly according to still another embodiment of the present invention, wherein the assembly includes an orthodontic appliance, a removable insert and an indirect bonding tray for facilitating bonding the appliance to a tooth surface.

An orthodontic assembly 20d according to another embodiment of the invention is illustrated in FIG. 12. The assembly 20d includes an appliance 22d and an indirect bonding tray 73d. The appliance 22d is similar to the appliance 22a illustrated in FIGS. 5–8.

The indirect bonding tray 73d includes an outer shell 78d and a matrix material 80d that is received in the shell 78d. The matrix material 80d includes a cavity 79d having a construction that matches at least a portion of the patient's dental arch.

At least one orthodontic appliance is releasably connected to the indirect bonding tray 73d. Preferably, a number of orthodontic appliances are releasably connected to the indirect bonding tray 73d so that a number of teeth can be bonded to appliances simultaneously. In FIG. 12, the illustrated appliance 22d is a bracket as described above in connection with appliance 22a, although other appliances such as buccal tubes, buttons and other attachments are also possible.

The appliance 22d includes a base 74d that preferably has a configuration that precisely matches a portion of the patient's tooth structure 64d. A quantity of a bonding adhesive 76d extends across the base 74d, and serves to fix the appliance 22d to the patient's tooth 64d with a bond having sufficient strength to resist unintended detachment from the tooth 64d during the course of treatment. Preferably, the bonding composition 76d is applied by the manufacturer to the base 74d before such time as the indirect bonding tray 73d is made and shipped to the practitioner.

A portion of the matrix material 80*d* extends into the channel of the appliance 22*d*. This channel is not shown in detail in FIG. 12, but is essentially the same as the channel 24*a* illustrated in FIG. 6. The portion of the matrix material 80*d* that extends in the channel provides an insert that prevents mesial and distal sections of the appliance 22*d* to be moved toward each other a distance that would otherwise be sufficient for debonding the appliance 22*d* from the tooth, similar in function to the insert 26*a* as described above.

Once the indirect bonding tray 73*d* is placed over the patient's tooth structure including tooth 64*d*, the bonding composition 76*d* is allowed to harden. Subsequently, the indirect bonding tray 73*d* is detached from the dental arch including the tooth 64*d* and is also detached from the appliances including appliance 22*d*, leaving the appliances affixed to respective teeth. As the tray 73*d* is detached from the appliance 22*d*, the portion of the matrix material 80*d* that was previously located within the channel of the appliance 22*d* is simultaneously removed from the channel. The appliance 22*d* can then be debonded from the tooth 64*d* when desired by moving one or both of the mesial and distal sections of the appliance 22*d* toward each other.

Further details of construction of the indirect bonding tray 73*d* are described in applicant's U.S. Pat. No. 7,020,963 and pending U.S. patent publication No. 2005/0074716, this disclosures of which are both hereby expressly incorporated by reference herein.

Figure 13:
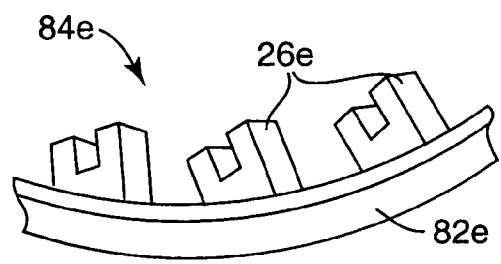
FIG. 13 is a fragmentary plan view illustrating another embodiment of the present invention, wherein a number of inserts for different appliances are integrally connected together.

FIG. 13 is an illustration of another embodiment of the invention, which includes a number of inserts 26*e* that are each similar to the inserts 26*a* described above. Each of the inserts 26*e* is integrally connected to an elongated, strip-like substrate 82*e* to present a single, unitary insert device 84*e*. Preferably, the space between adjacent inserts 26*e* is equal to the spacing between channels of adjacent appliances when the appliances are mounted on the patient's teeth.

Preferably, the insert device 84*e* is received in the channels of all or at least a majority of all of the appliances mounted on a patient's dental arch. As an example, the insert 84*e* may be used in instances where the appliances are covered by a plastic repositioning tray (such as the tray 60*b* mentioned above). When the portion of orthodontic treatment using the tray has concluded, the tray is removed from the dental arch to uncover the insert device 84*e*. Next, the practitioner can detach the insert device 84*e* from all of the appliances in a single step before an archwire is inserted in the archwire slots of the appliances. The insert device 84*e* provides a timesaving to the practitioner, in that each of the inserts for each corresponding appliance need not be removed in separate, sequential steps.

Optionally, the insert device 84*e* may be connected to the positioning tray. For example, the insert device 84*e* as it appears in FIG. 13 may be adhesively bonded to the inner walls of the positioning tray. As another option, the insert device 84*e* may be integrally molded with the inner walls of the positioning tray.

Preferably, the substrate 82*e* and the inserts 26*e* are made of aesthetically pleasing transparent or translucent materials, such as the polymeric materials described in the paragraphs above.

The examples described herein and illustrated in the accompanying drawings are intended to be illustrative of the invention. The invention should not be deemed limited to the specific examples described in detail, but instead only by a fair scope of the claims that follow along with their equivalents.

The invention claimed is:

1. An assembly comprising:
    a ceramic orthodontic appliance having a base for bonding the appliance to a tooth and a body extending outwardly from the base, the body including a first section, a second section and an elongated channel extending between the first section and the second section, the appliance including a frangible web beneath the channel that fractures to debond the appliance from the tooth when at least one of the first section and the second section is moved in a direction toward the channel; and
    an insert removably received in the channel, the insert substantially preventing movement of the first section and the second section to an extent sufficient to fracture the web and debond the appliance from the tooth when the insert is received in the channel.

2. An assembly according to claim 1 wherein the insert has a generally flat shape.

3. An assembly according to claim 1 wherein the insert is made of a material that transmits light.

4. An assembly according to claim 3 wherein the insert is made of a plastic material.

5. An assembly according to claim 1 wherein the appliance is a bracket having at least one tiewing.

6. An assembly according to claim 1 wherein the appliance is a bracket having an archwire slot extending in a generally mesial-distal direction.

7. An assembly according to claim 6 wherein the channel extends in a generally occlusal-gingival direction.

8. An assembly according to claim 1 and including a tray releasably coupled to the appliance, wherein the tray has at least one cavity for receiving a tooth.

9. An assembly according to claim 8 wherein the tray includes a receptacle for receiving the appliance.

10. An assembly according to claim 9 wherein the tray is a resilient repositioning tray.

11. An assembly according to claim 10 wherein the tray is one tray of a series of trays, and wherein each tray is constructed to reposition the teeth in incremental steps.

12. An assembly according to claim 10 wherein the insert is connected to the tray.

13. An assembly according to claim 8 wherein the tray is an indirect bonding tray.

14. An assembly according to claim 13 wherein the insert is connected to the tray.

15. An assembly according to claim 1 wherein the appliance, the insert and the tray are made of materials that transmit light.

16. An assembly according to claim 1 wherein the channel extends in a generally mesial-distal direction.

17. An assembly according to claim 1 wherein the direction is a direction that extends in an arc about a reference axis extending generally parallel to the longitudinal axis of the channel.

18. An assembly according to claim 1 wherein the direction is a direction that extends generally along a mesial-distal reference axis.

19. An assembly according to claim 1 wherein the insert includes structure for positioning the appliance relative to the patient's tooth.

20. An assembly according to claim 19 wherein the structure comprises a leg for contact with an occlusal edge of the patient's tooth.

21. A method of orthodontic treatment comprising:
    bonding an appliance to a patient's tooth, wherein the appliance has a first section, a second section and an elongated channel extending between the first section and the second section;
    applying force to the appliance in order to move the tooth toward a desired position;

removing an insert from the channel after the tooth has been at least partially moved toward the desired position; and debonding the appliance from the patient's tooth by moving at least one of the first section and the second section in a direction generally toward the channel.

22. A method of orthodontic treatment according to claim 21 wherein the act of removing the insert from the channel is carried out prior to the act of applying force to the appliance.

23. A method of orthodontic treatment according to claim 21 wherein the act of bonding the appliance to a tooth is carried out by using an indirect bonding tray.

24. A method of orthodontic treatment according to claim 23 wherein the insert is connected to the tray, wherein the method includes the act of detaching the tray from the tooth, and wherein the act of removing the insert is carried out simultaneously with detachment of the tray from the tooth.

25. A method of orthodontic treatment according to claim 21 wherein the act of removing the insert from the channel is carried out subsequent to at least a portion of the act of applying force to the appliance.

26. A method of orthodontic treatment according to claim 21 wherein the act of applying force is carried out at least in part by a resilient repositioning tray.

27. A method of orthodontic treatment according to claim 21 wherein the act of applying force is carried out in part by a resilient repositioning tray and in part by an archwire that is connected to the appliance.

28. A method of orthodontic treatment according to claim 27 and including the act of detaching the tray from the tooth, wherein the act of applying force in part by the archwire is carried out subsequent to the act of detaching the tray from the tooth.

29. A method of orthodontic treatment according to claim 21 wherein the act of bonding an appliance to a patient's tooth includes the act of positioning the appliance relative to the tooth using the insert as a positioning jig.

30. A method of orthodontic treatment according to claim 29 wherein the act of positioning the appliance includes the act of placing a leg of the insert against an occlusal edge of the tooth.

* * * * *

UNITED STATES PATENT AND TRADEMARK OFFICE
CERTIFICATE OF CORRECTION

| | | |
|---|---|---|
| PATENT NO. | : 7,153,130 B2 | Page 1 of 1 |
| APPLICATION NO. | : 10/865434 | |
| DATED | : December 26, 2006 | |
| INVENTOR(S) | : James D. Christoff | |

It is certified that error appears in the above-identified patent and that said Letters Patent is hereby corrected as shown below:

<u>Column 10</u>
Line 43, In Claim 15, delete "1" and insert --8-- therefore.

Signed and Sealed this

Sixth Day of March, 2007

JON W. DUDAS
*Director of the United States Patent and Trademark Office*